United States Patent
Van Der Wal et al.

(10) Patent No.: US 12,285,201 B2
(45) Date of Patent: *Apr. 29, 2025

(54) TOOL SYSTEM FOR REMOVING PROSTHETIC CEMENT FROM A BONE OF A PATIENT UNDERGOING A JOINT PROSTHESIS REPLACEMENT OPERATION

(71) Applicant: UMC UTRECHT HOLDING B.V., Utrecht (NL)

(72) Inventors: Bart Cornelis Hendrikus Van Der Wal, Utrecht (NL); Henri Charles Vogelij, Utrecht (NL); Hermannus Hendricus Weinans, Utrecht (NL); Lucas Alphonsus Maria Evers, Utrecht (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/486,437

(22) Filed: Oct. 13, 2023

(65) Prior Publication Data

US 2024/0108390 A1 Apr. 4, 2024

Related U.S. Application Data

(63) Continuation of application No. 16/973,466, filed as application No. PCT/EP2019/066782 on Jun. 25, 2019, now Pat. No. 11,801,080.

(30) Foreign Application Priority Data

Jun. 27, 2018 (NL) ...................................... 2021191

(51) Int. Cl.
*A61B 17/14* (2006.01)
*A61B 17/15* (2006.01)
(Continued)

(52) U.S. Cl.
CPC ........ *A61B 17/8847* (2013.01); *A61B 17/149* (2016.11); *A61B 17/15* (2013.01); *A61F 2/4607* (2013.01)

(58) Field of Classification Search
CPC ........... A61F 2/4607; A61F 2002/4619; A61B 17/155; A61B 17/8847; A61B 17/149
See application file for complete search history.

(56) References Cited

U.S. PATENT DOCUMENTS 4,846,161 A * 7/1989 Roger ................ A61B 17/8847
606/82
4,986,826 A 1/1991 Roger
(Continued)

FOREIGN PATENT DOCUMENTS

| EP | 0552578 A1 | 7/1993 |
| EP | 2057950 A2 | 5/2009 |
| GB | 110179 A | 10/1917 |

OTHER PUBLICATIONS

International Search Report and Written Opinion for the International Patent Application No. PCT/EP2019/066782, mailed Jan. 8, 2020, 18 pages.

*Primary Examiner* — Nicholas W Woodall
(74) *Attorney, Agent, or Firm* — KDW Firm PLLC

(57) ABSTRACT

A method for providing a tool system for removing prosthetic cement from a bone of a patient undergoing a joint prosthesis replacement operation includes scanning the patient in the area of the joint prosthesis to obtain a profile of a line of intersection of a prosthetic cement/bone interface at its intersection with a longitudinally pre-selected plane; providing a guide member shaped as a stem of the prosthesis in a prosthetic cavity located in said prosthetic cement; and providing a cutting tool for forming a running cut through the prosthetic cement along the line of intersection. A stem of the cutting tool includes two protrusions along the length
(Continued)

thereof. A guide member includes two grooves which each engage one of said protrusions. Grooves are profiled so the outer end of the stem is forced to follow a path corresponding to the profile of the line of intersection of the cement/bone interface.

11 Claims, 16 Drawing Sheets

(51) Int. Cl.
    *A61B 17/88*     (2006.01)
    *A61F 2/46*     (2006.01)

(56) References Cited

U.S. PATENT DOCUMENTS

| | | |
|---|---|---|
| 5,047,035 A | 9/1991 | Mikhail |
| 5,725,530 A | 3/1998 | Popken |
| 6,187,012 B1 * | 2/2001 | Masini .................. A61F 2/4607 606/99 |
| 9,603,720 B2 * | 3/2017 | Kelley ................. A61B 17/155 |
| 9,867,628 B2 * | 1/2018 | Macke ............... A61B 17/1742 |
| 11,801,080 B2 * | 10/2023 | Van Der Wal ......... A61B 17/15 |
| 2012/0116406 A1 * | 5/2012 | Talamini ................ A61B 17/15 606/88 |
| 2015/0216578 A1 * | 8/2015 | Lenaerts ............ G05B 19/4097 700/98 |

\* cited by examiner

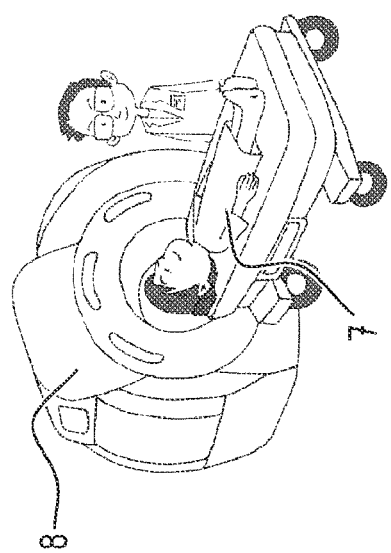
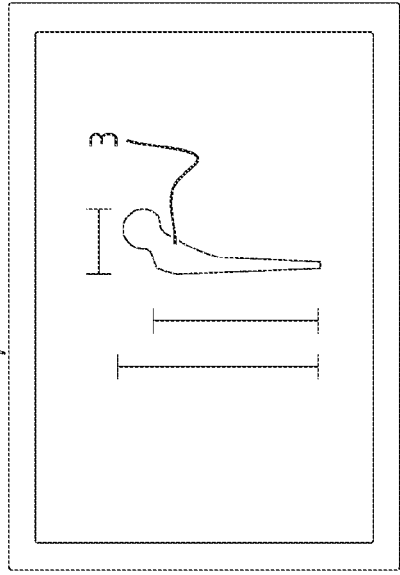
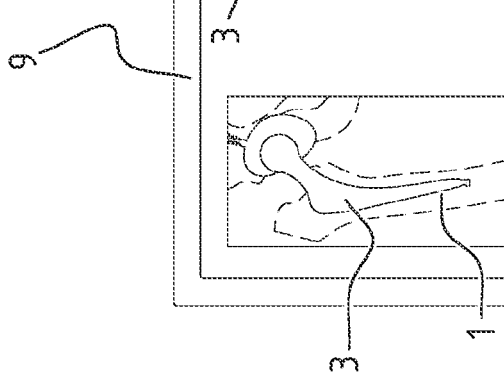
FIG. 2A
FIG. 1
FIG. 2B

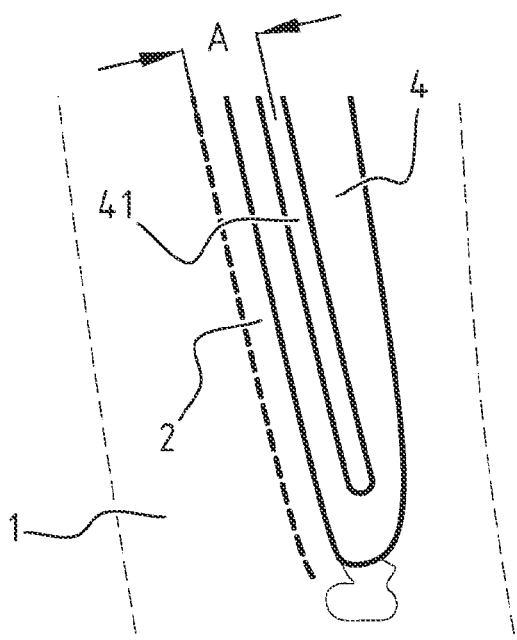
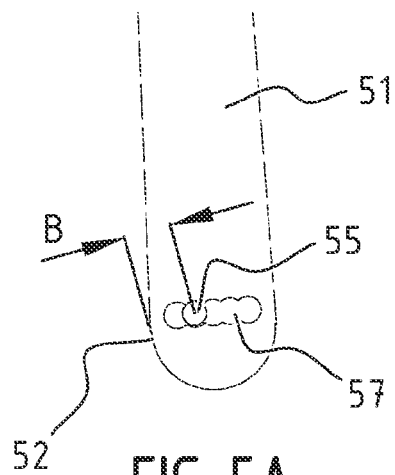
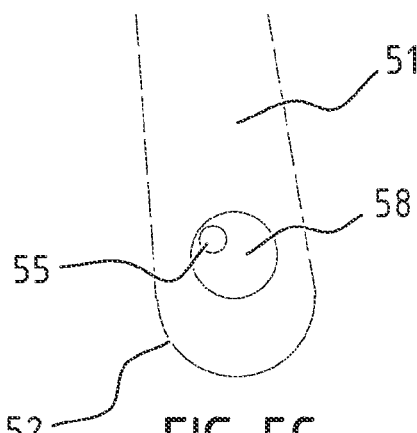
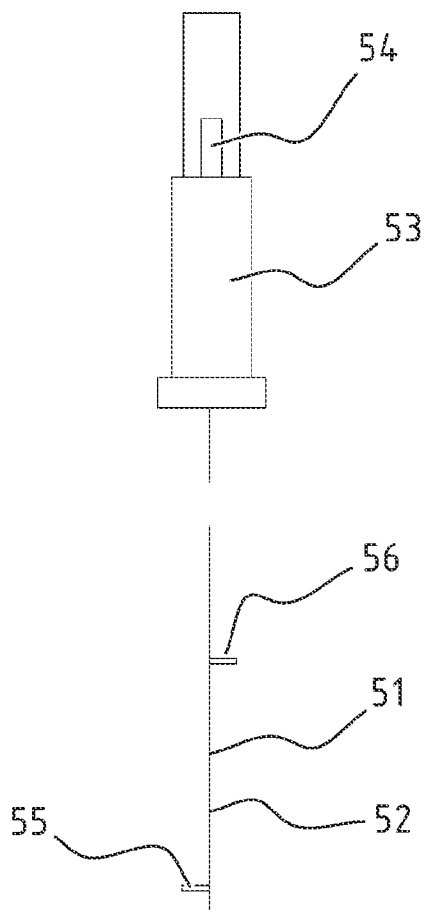
FIG. 4
FIG. 5A
FIG. 5B
FIG. 5C

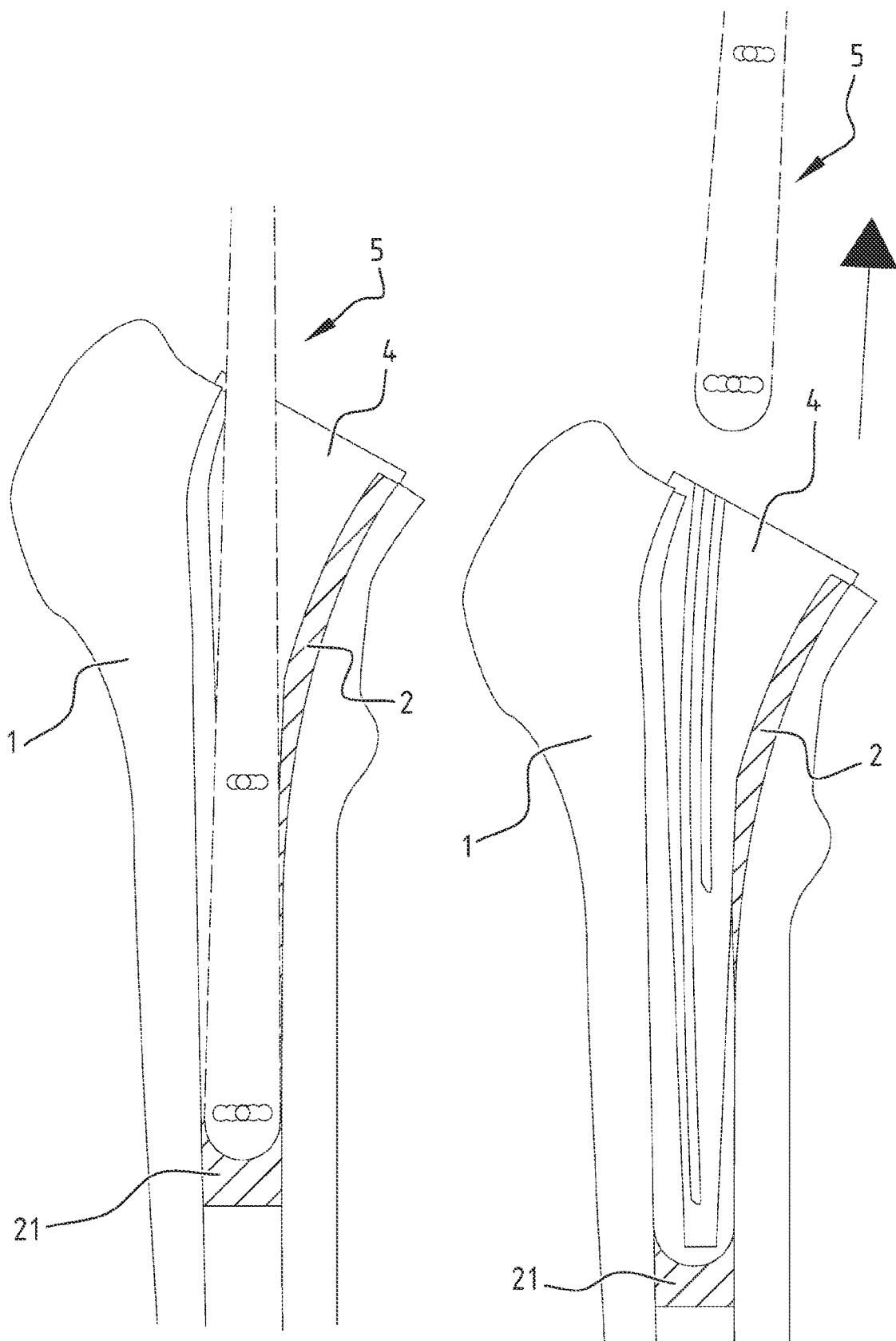

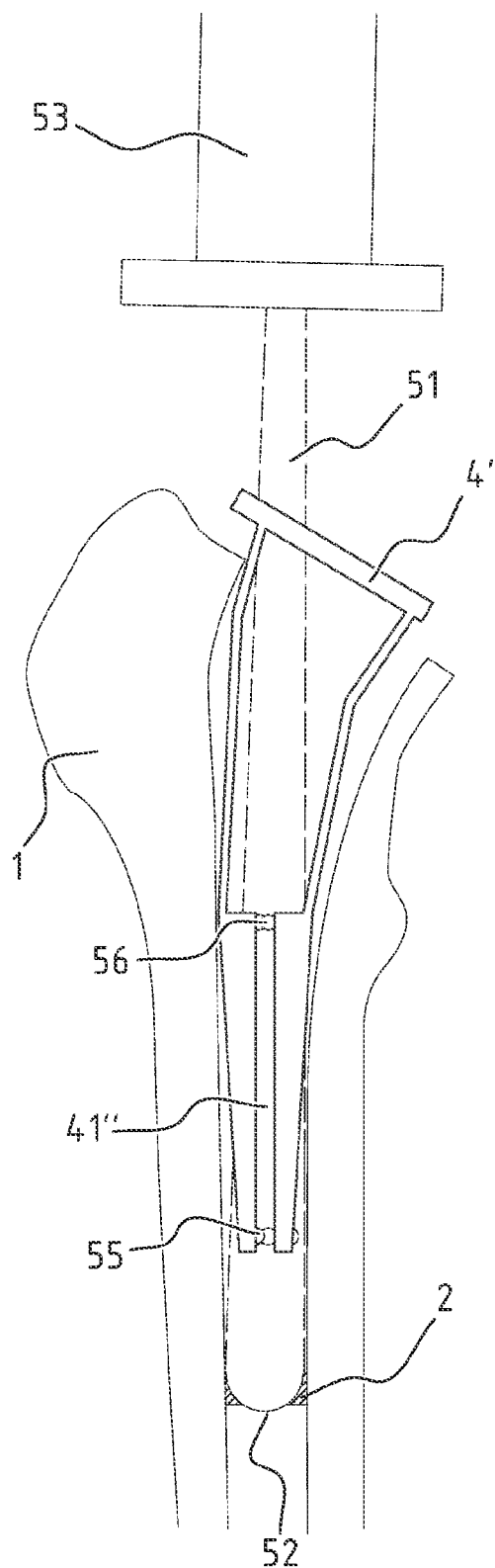
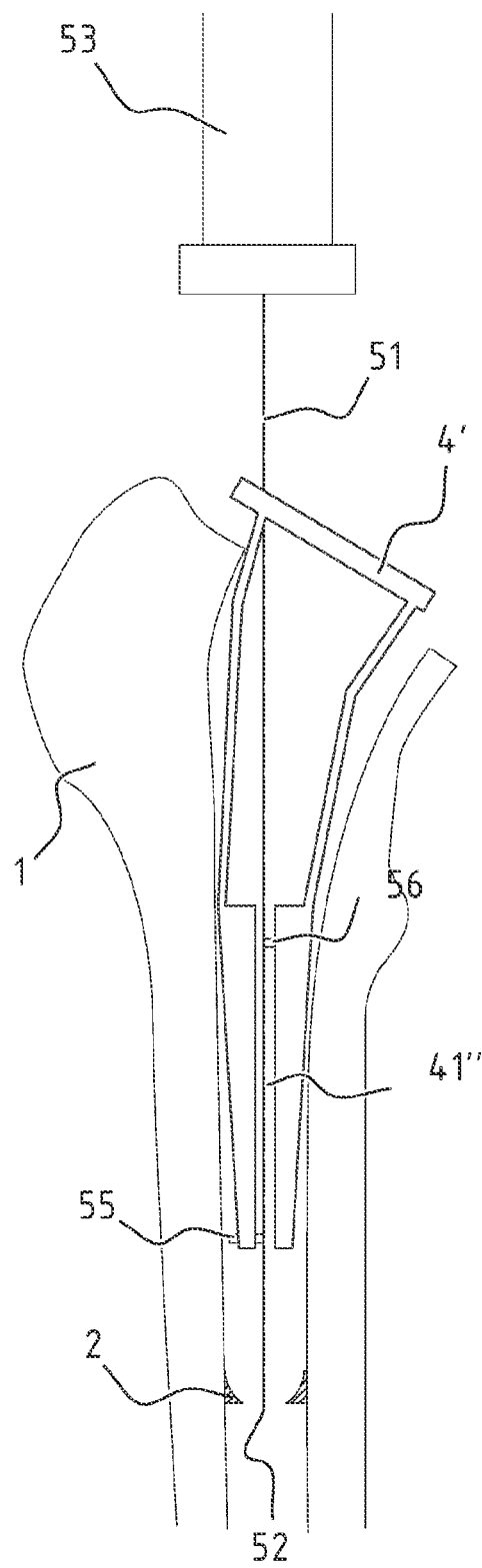
FIG. 7E
FIG. 7F

TOOL SYSTEM FOR REMOVING PROSTHETIC CEMENT FROM A BONE OF A PATIENT UNDERGOING A JOINT PROSTHESIS REPLACEMENT OPERATION

CROSS-REFERENCE TO RELATED APPLICATION

This is a continuation of U.S. nonprovisional patent application Ser. No. 16/973,466, filed Dec. 9, 2020, which is a national stage filing under 35 U.S.C. 371 of international patent application PCT/EP2019/066782, filed Jun. 25, 2019, and Netherlands Patent application serial number NL2021191, filed Jun. 27, 2018, the entirety of which applications are incorporated by reference herein.

The invention relates to a method for providing a tool system for removing prosthetic cement from a bone of a patient undergoing a joint prosthesis replacement operation. The method comprises the steps of: scanning the patient in the area of the joint prosthesis so as to obtain at least one profile of a line of intersection of a prosthetic cement/bone interface at its intersection with a generally longitudinally pre-selected plane; providing a guide member substantially shaped as a stem of the prosthesis in a prosthetic cavity located in said prosthetic cement; providing a cutting tool for forming a running cut substantially completely through the prosthetic cement along the line of intersection. Such a method is described in the international patent application publication no. WO 87/02571, which is incorporated herein by reference.

Although the tool system will be most often used for removing a cemented stem in hip revision surgery, the method can also be used to remove a cemented stem in shoulder revision surgery, or other cemented bone implant removals.

Removal of a well-fixed implant in cemented total hip arthroplasty can be very challenging. Indications for removing a well-fixed implant may include sepsis, recurrent dislocation due to femoral component malposition and/or inadequate offset. Attempting to remove a well-fixed implant from proximal exposure alone can result in extensive bone loss due to the inability to disrupt the bone/prosthesis interface distally. One of the most difficult aspects of Revision Total Hip Replacement (RTHR) surgery is that the surgeon may have very limited information about the location and amount of bone cement in the femur during the surgical procedure. The perforation and fracture of the femur during the removal of bone cement in revision total hip arthroplasty (THA) are serious complications that considerably affect the postoperative protocols and clinical results.

The extended trochanteric osteotomy is the most common osteotomy used in cemented femoral revision and allows improved access to the implant/bone or implant/cement interface.

Indications for the extended proximal femoral osteotomy include revision of well-fixed cemented femoral components or removal of a loose femoral stem with a well-bonded cement mantle. The use of an extended trochanteric osteotomy in these situations will minimize intraoperative complications and will result in predictable healing. However, comparison of surgeries with and without osteotomy clearly show that trochanteric osteotomy prolongs the surgery, is associated with more blood loss, and causes a slower postoperative rehabilitation course. Besides that, additional fractures (20%), nonunions (1.2%), 1 malunion (0.6%), and reoperations (10.2%) are reported.

Bone cement can be safely removed using the known ROBODOC system, which uses high speed milling. No serious complications have been reported using this system and full weight bearing is achieved early in the postoperative course because of circumferential preservation of the femoral cortex. However this system is expensive and time consuming because of the need to implant locater pins before the revision surgery and a mean robotic milling time of 34 min (range 17-51 min). Besides that there is a risk of heat injury during the ROBODOC milling process of cement removal.

The invention aims at an improved method, preferably resulting in a shortened surgical time, a reduced morbidity, a decreased blood loss, less fractures and/or less reoperations.

To that end the method in accordance with the invention is characterized in that the cutting tool comprises: an elongated stem having dimensions to be inserted into the prosthetic cavity at least substantially to the bottom end thereof; a driven cutting element arranged on said stem and arranged to cut the prosthetic cement at one outer end of said stem; a grip arranged on the other outer end of said stem for engagement of the cutting tool by an operator; wherein the stem of the cutting tool comprises two laterally extending protrusions, which protrusions are located along the length of the stem at a mutual distance apart; and wherein the guide member is provided with two longitudinally running grooves which each are arranged to engage one of said protrusions of the cutting tool, wherein the grooves are profiled such that the outer end of the stem at which the cutting element is arranged to cut the prosthetic cement, when inserted into the prosthetic cavity and being moved to at least substantially to the bottom end thereof, is forced to follow a path corresponding to the profile of the line of intersection of the cement/bone interface.

Preferably the stem comprises a chainsaw blade and the cutting element comprises a driven cutting chain, provided with the two laterally extending protrusions on the chainsaw blade. More preferably the cutting tool is a small electrical chainsaw, such as a Bosch™ NanoBlade™-type chainsaw, provided with the two laterally extending protrusions on the chainsaw blade. Preferably the protrusions are pins.

Preferably the position of at least one of the protrusions on the chainsaw blade is adaptable in the direction of the side edges of the chainsaw blade, so as to accommodate for both relatively deep and shallow cement cuts. Preferably the chainsaw blade has a wedge shape, wherein the outer end where the cutting chain is arranged to cut is the widest end of the wedge shaped chainsaw blade. Preferably the protrusions extend laterally on opposite sides of the blade, and the grooves are provided in corresponding opposite sides of the guide member.

Preferably the longitudinally running grooves are substantially U-, V- or Y-shaped, wherein the grooves are profiled such that the outer cutting end of cutting element, when inserted into the prosthetic cavity and being moved to at least substantially to the bottom end thereof, wherein the protrusions move through first ones of said legs of said U-, V- or Y-shaped grooves, and back to the upper end thereof, wherein the protrusions move through the other legs of said U-, V- or Y-shaped grooves, is forced to follow a substantially U-shaped path corresponding to the profile of the line of intersection of the cement/bone interface on two opposite sides of the intersection.

Preferably said guide member is produced by means of a 3D-printer. Preferably the profiles of said grooves are calculated from said profile of said line of intersection of the prosthetic cement/bone interface by means of a computer loaded with a computer program comprising instructions to carry out said calculation. Preferably said 3D-printer is controlled by said computer loaded with said computer program, said computer program further comprising instructions to control said 3D-printer.

The invention also relates to a cutting tool for use in a method for removing prosthetic cement from a bone of a patient undergoing a joint prosthesis replacement operation, comprising: an elongated stem having dimensions to be inserted into a prosthetic cavity located in prosthetic cement at least substantially to the bottom end thereof; a cutting element arranged on said stem and arranged to cut prosthetic cement at one outer end of said stem; a grip arranged on the other outer end of said stem for engagement of the cutting tool by an operator; wherein the stem of the cutting tool comprises two laterally extending protrusions, which protrusions are located along the length of the stem at a mutual distance apart, each one of said protrusions being arranged for engagement by a groove of a guide member such that the outer end of the stem at which the cutting element is arranged to cut the prosthetic cement is forced to follow a predetermined path.

Furthermore the invention relates to a guide member for use in a method for removing prosthetic cement from a bone of a patient undergoing a joint prosthesis replacement operation, said guide member being produced by the steps of: scanning the patient in the area of the joint prosthesis so as to obtain at least one profile of a line of intersection of a prosthetic cement/bone interface at its intersection with a generally longitudinally pre-selected plane; providing a guide member substantially shaped as a stem of the prosthesis in a prosthetic cavity located in said prosthetic cement; wherein the guide member is provided with two longitudinally running grooves which each engage one of said protrusions of the cutting tool, wherein the grooves are profiled such that the outer end of the stem at which the cutting element is arranged to cut the prosthetic cement is forced to follow a path corresponding to the profile of the line of intersection of the cement/bone interface.

The invention also relates to a method for removing prosthetic cement from a bone of a patient undergoing a joint prosthesis replacement operation, comprising the steps of: scanning the patient in the area of the joint prosthesis so as to obtain at least one profile of a line of intersection of a prosthetic cement/bone interface at its intersection with a generally longitudinally pre-selected plane; providing a guide member substantially shaped as a stem of the prosthesis in a prosthetic cavity located in said prosthetic cement; removing the prosthesis to be replaced from the prosthetic cavity; positioning the guide member in the prosthetic cavity for guiding a cutting tool along the guide member to form a running cut substantially completely through the prosthetic cement along the line of intersection and guiding the cutting tool along the guide member to form said cut substantially without cutting the adjacent bone; removing remaining prosthetic cement from the bone; wherein the cutting tool comprises an elongated stem having dimensions to be inserted into the prosthetic cavity at least substantially to the bottom end thereof; a cutting element arranged on said stem and arranged to cut the prosthetic cement at one outer end of said stem; a grip arranged on the other outer end of said stem for engagement of the cutting tool by an operator; wherein the stem of the cutting tool comprises two laterally extending protrusions, which protrusions are located along the length of the stem at a mutual distance apart; wherein the guide member is provided with two longitudinally running grooves which each engage one of said protrusions of the cutting tool, wherein the grooves are profiled such that the outer end of the stem at which the cutting element is arranged to cut the prosthetic cement is forced to follow a path corresponding to the profile of the line of intersection of the cement/bone interface.

Preferably the method further comprises the steps of repeating at least once the following steps along the line of intersection of one or more other generally longitudinal pre-selected planes of the joint prosthesis cavity and the associated cement/bone interface of the patient to form a number of segmented prosthetic cement pieces, before removing remaining prosthetic cement from the bone: providing a further guide member substantially shaped as a stem of the prosthesis in the prosthetic cavity located in said prosthetic cement, wherein the guide member is provided with two longitudinally running grooves which each engage one of said protrusions of the cutting tool; wherein the grooves are profiled such that the outer end of the stem at which the cutting element is arranged to cut the prosthetic cement is forced to follow a path corresponding to the profile of the line of intersection of the cement/bone interface; positioning the guide member in the prosthetic cavity for guiding the cutting tool along the guide member to form a running cut substantially completely through the prosthetic cement along the line of intersection and guiding the cutting tool along the guide member to form said cut substantially without cutting the adjacent bone.

Preferably, before or after said removing remaining prosthetic cement from the bone the method further comprises the steps of: positioning a further guide member substantially shaped as a stem of the prosthesis in the prosthetic cavity located in said prosthetic cement, wherein the guide member is provided with two longitudinally running grooves which each engage one of said protrusions of the cutting tool; wherein the grooves are profiled such that the outer end of the stem at which the cutting element is arranged to cut the prosthetic cement is forced to follow a path deeper into the prosthetic cavity in order to cut through a bottom cement plug present in said cavity; removing the remaining prosthetic cement pieces of said plug.

Preferably said remaining prosthetic cement pieces of said plug are removed by means of a tool comprising an elongated stem having dimensions to be inserted into the prosthetic cavity at least substantially to the bottom of the remaining prosthetic cement pieces of said plug, a hook arranged on said stem and arranged to be inserted through said cut or cuts through the bottom cement plug, and a grip arranged on the other outer end of said stem for engagement of the tool by an operator and/or a hammer, wherein said hook is inserted through said cut or cuts until the hook extends below said pieces of said plug, wherein said stem is rotated around its axis such that the hook is allowed to engage the bottom surface of said pieces, and wherein the stem is forcibly moved out of the prosthetic cavity, thereby removing said remaining pieces of said plug. Preferably said hook has a X-shaped cross section, seen from the bottom, such that the hook can be inserted through an X-shaped opening in the bottom cement plug made by at least two of said cuts, such that all of the remaining four pieces of said plug can be engaged and removed at once.

The invention also relates to a tool comprising an elongated stem having dimensions to be inserted into a prosthetic cavity at least substantially to the bottom of remaining prosthetic cement pieces of a plug in said cavity after said plug has been cut, a hook arranged on said stem and arranged to be inserted through a cut or cuts through the bottom cement plug, and a grip arranged on the other outer end of said stem for engagement of the tool by an operator and/or a hammer. Preferably said hook has a X-shaped cross section, seen from the bottom.

In a preferred method of the invention a number, usually 4, of longitudinal cuts are produced in the prosthetic cement spaced apart about the cavity and produced by the above method.

The invention will now explained in more detail by means of exemplary embodiments, as shown in the figures, wherein:

FIG. 1 is a perspective view of a CT scanner in which the prosthesis and the femur of a patient with a cemented total hip arthroplasty, which should undergo revision surgery, is being scanned;

FIG. 2A is a front view of a computer screen on which a CT scan (left) and a virtual 3D model (right) of the prosthesis and the bone cement and is shown;

FIG. 2B is a front view of a computer screen on which the prosthesis and its dimensions is shown;

Figure 3C:
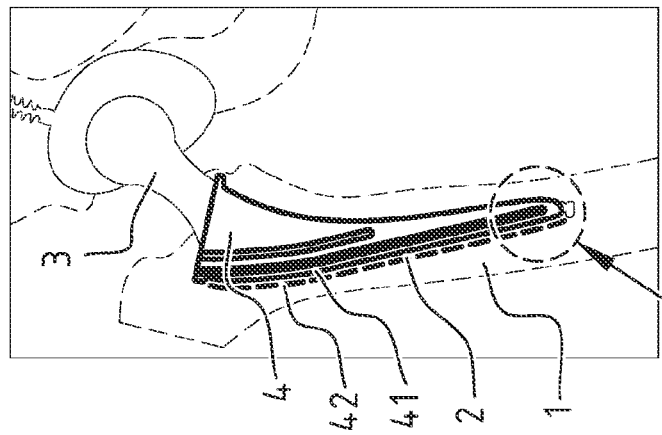
Figure 3B:
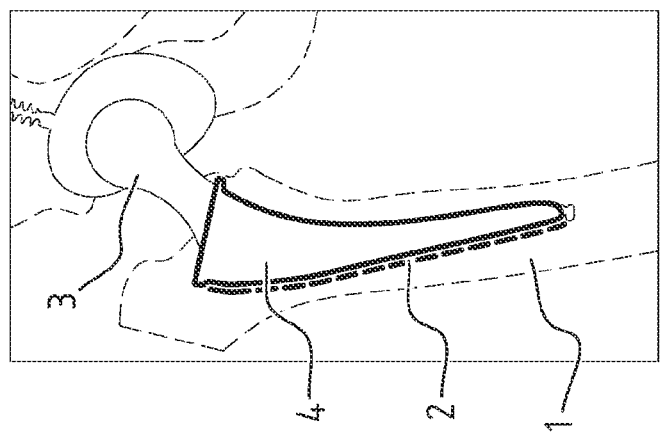
Figure 3A:
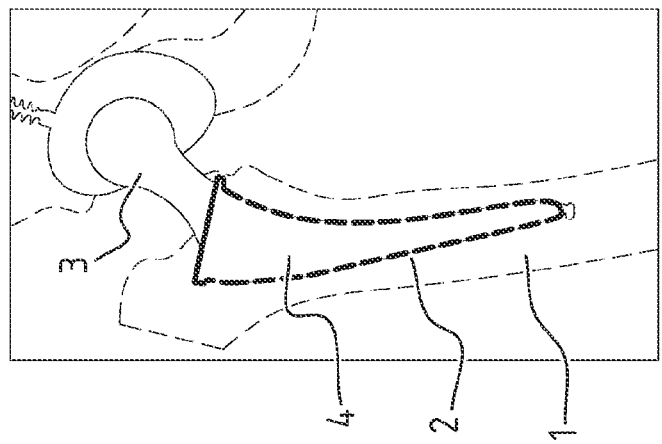
Figures 6A, 6B:
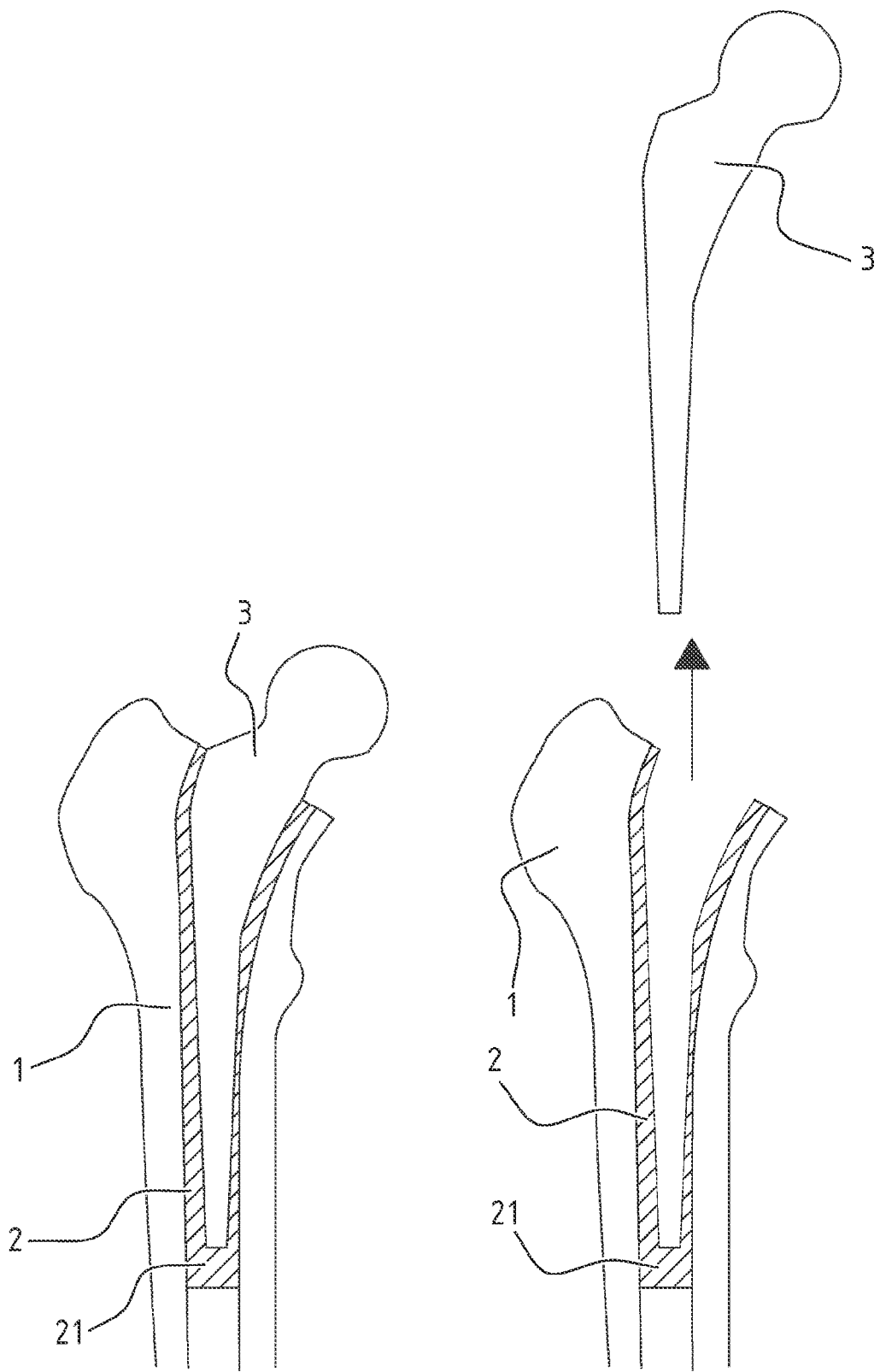
Figure 6C:
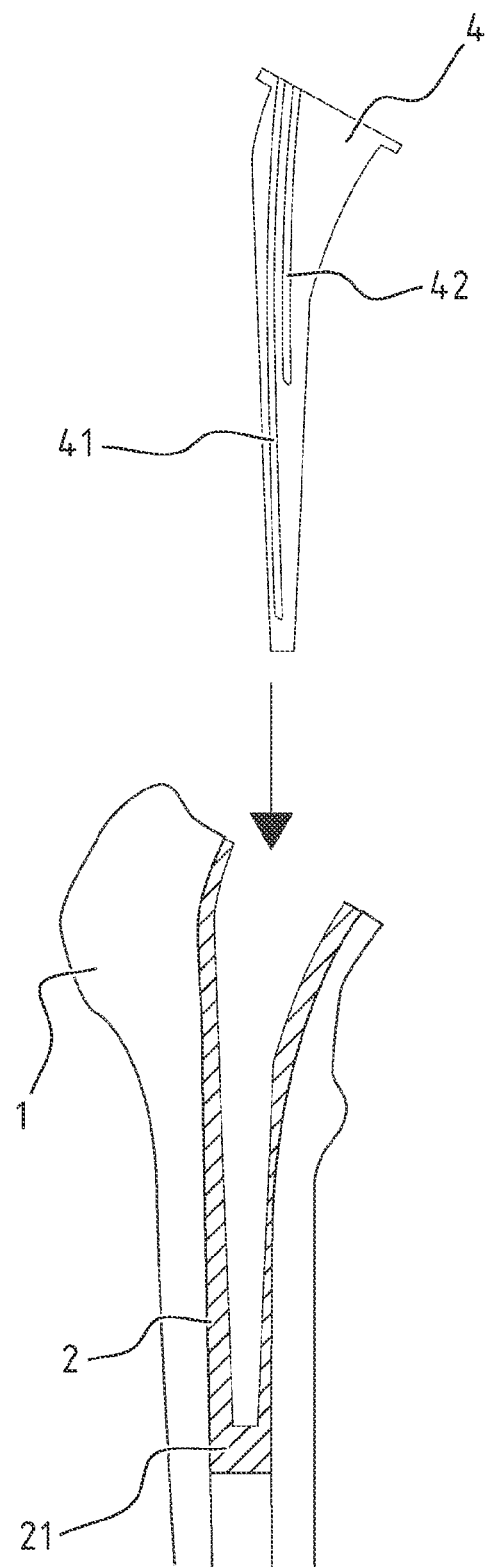
Figure 6D:
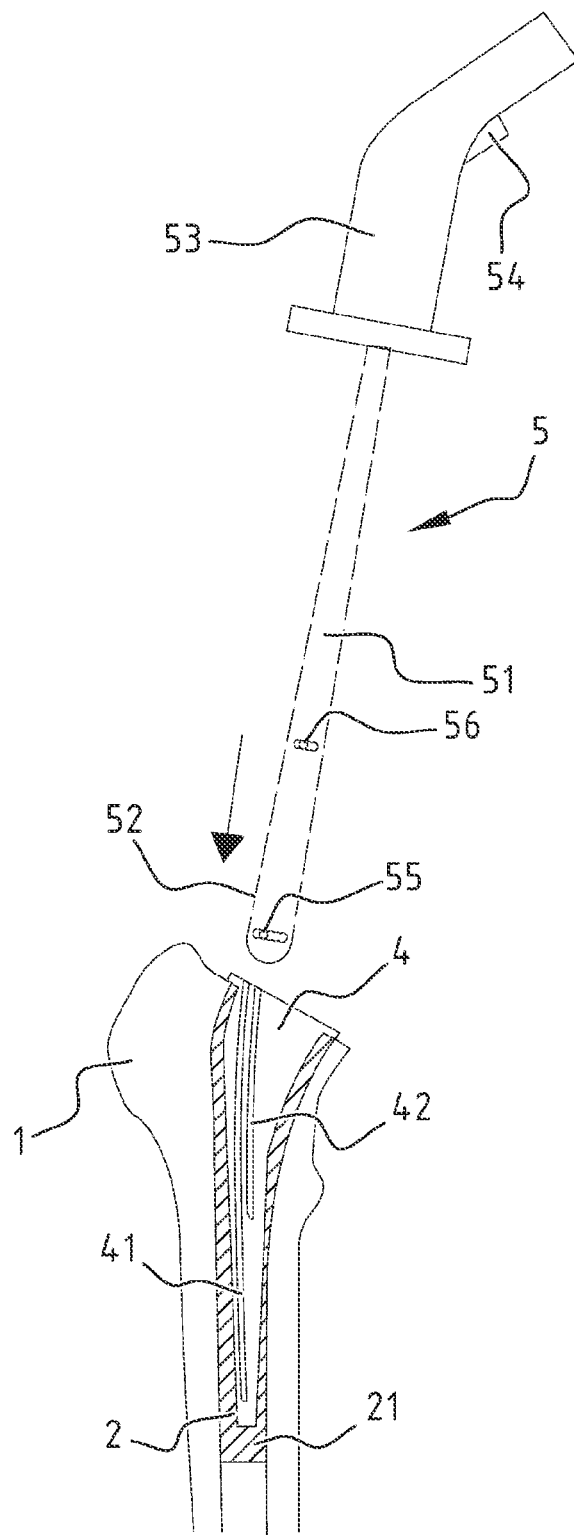
Figures 6E, 6F:
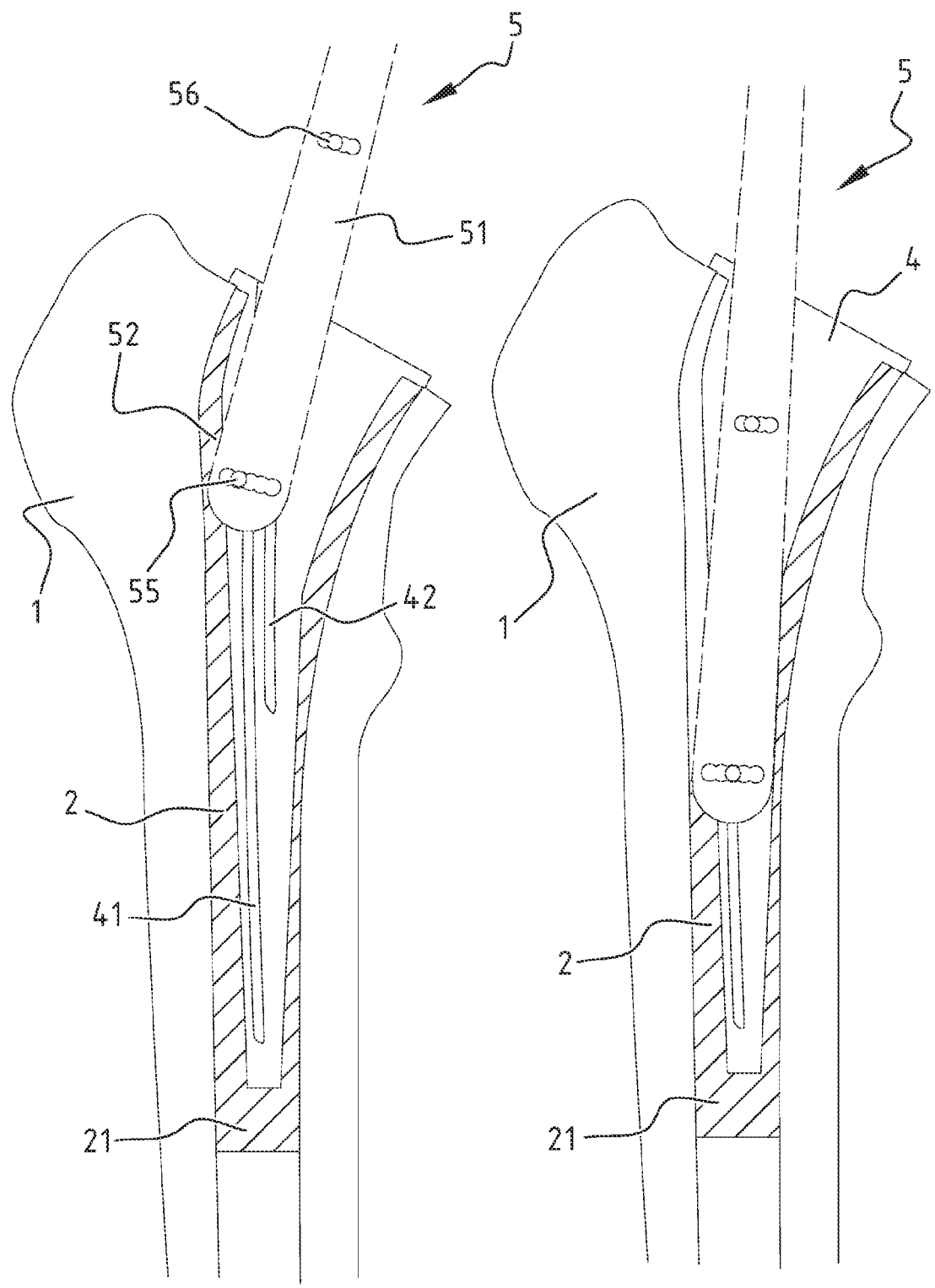
Figure 6I:
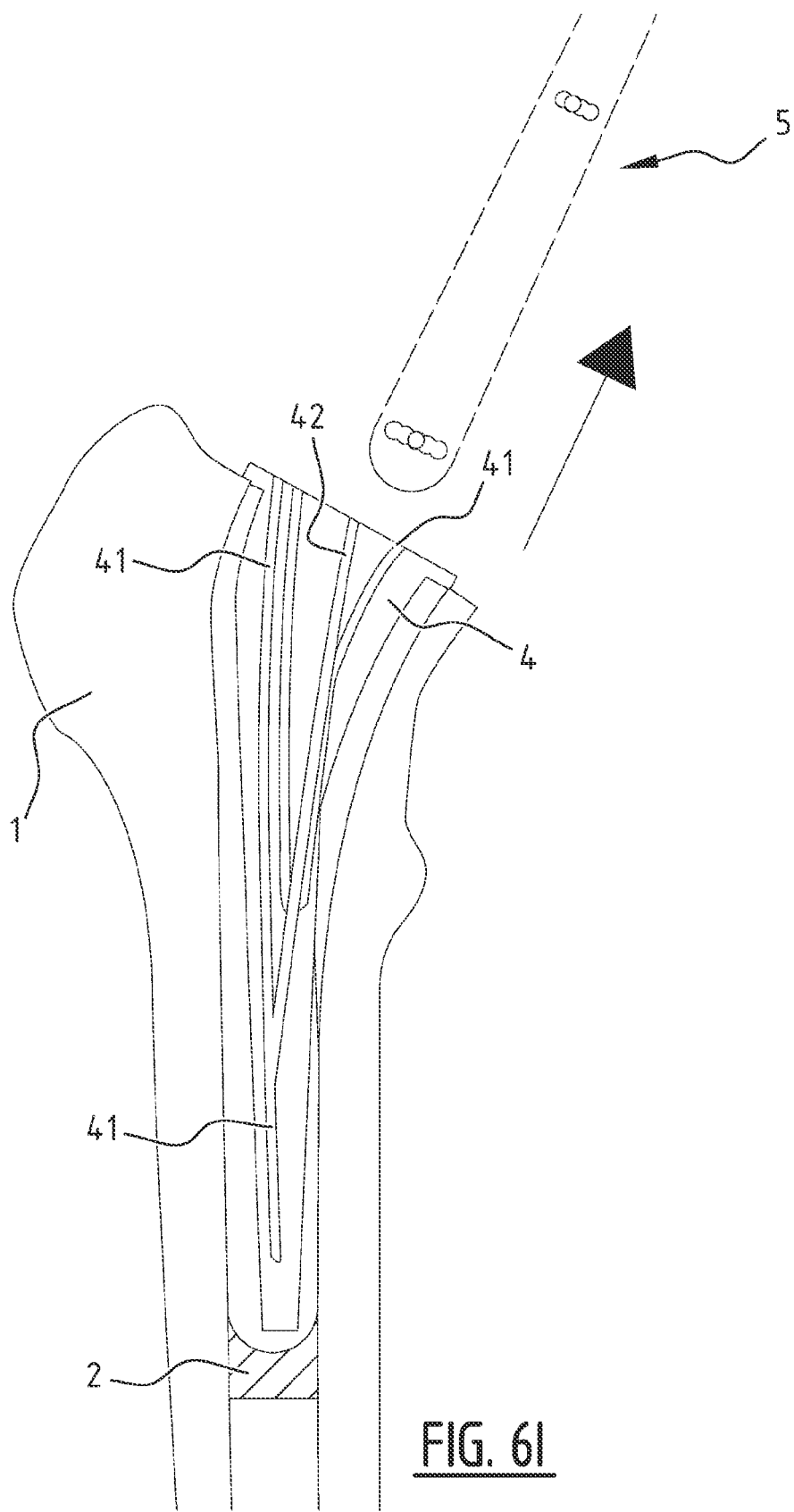
Figures 7A, 7B:
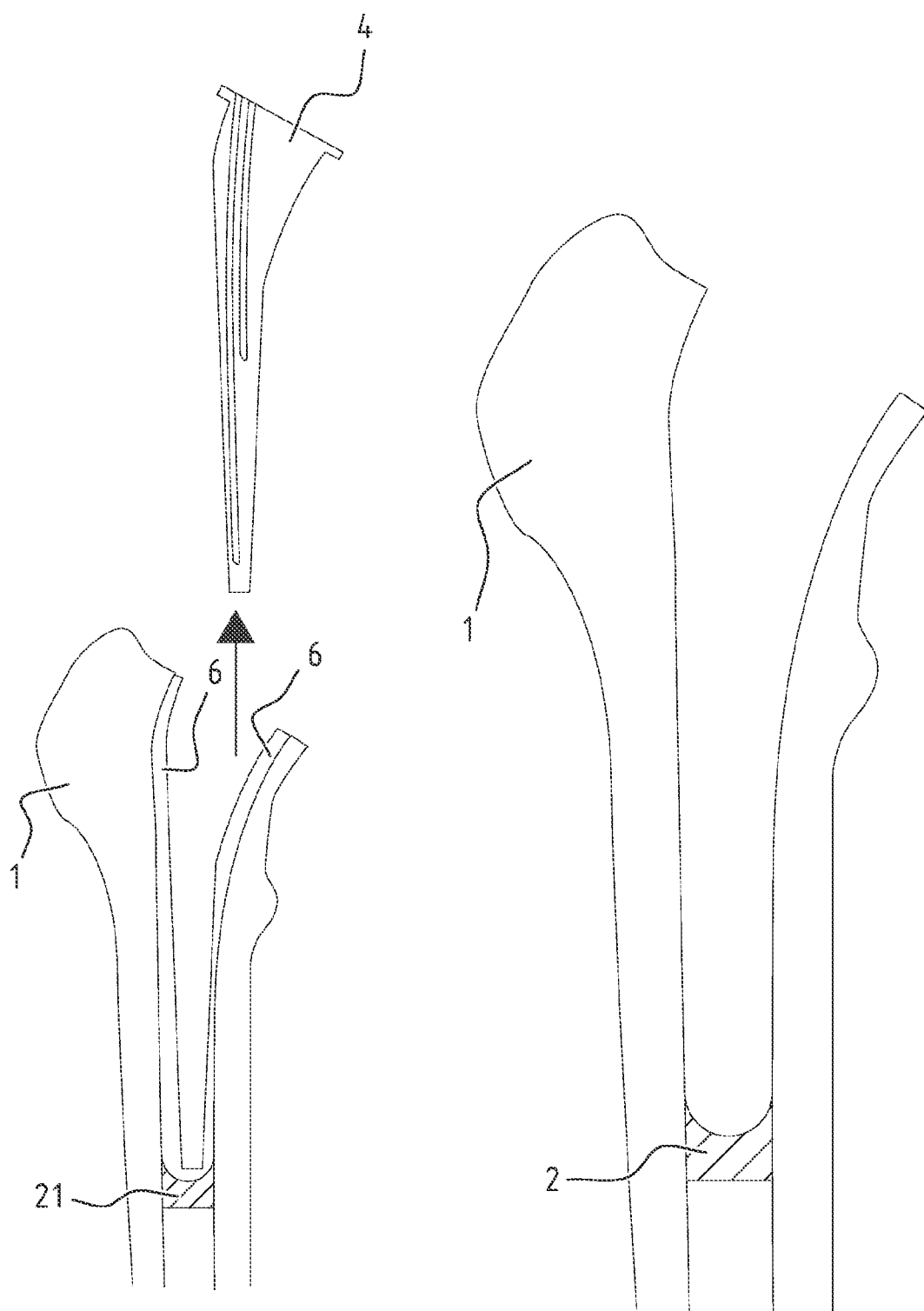
Figures 7C, 7D:
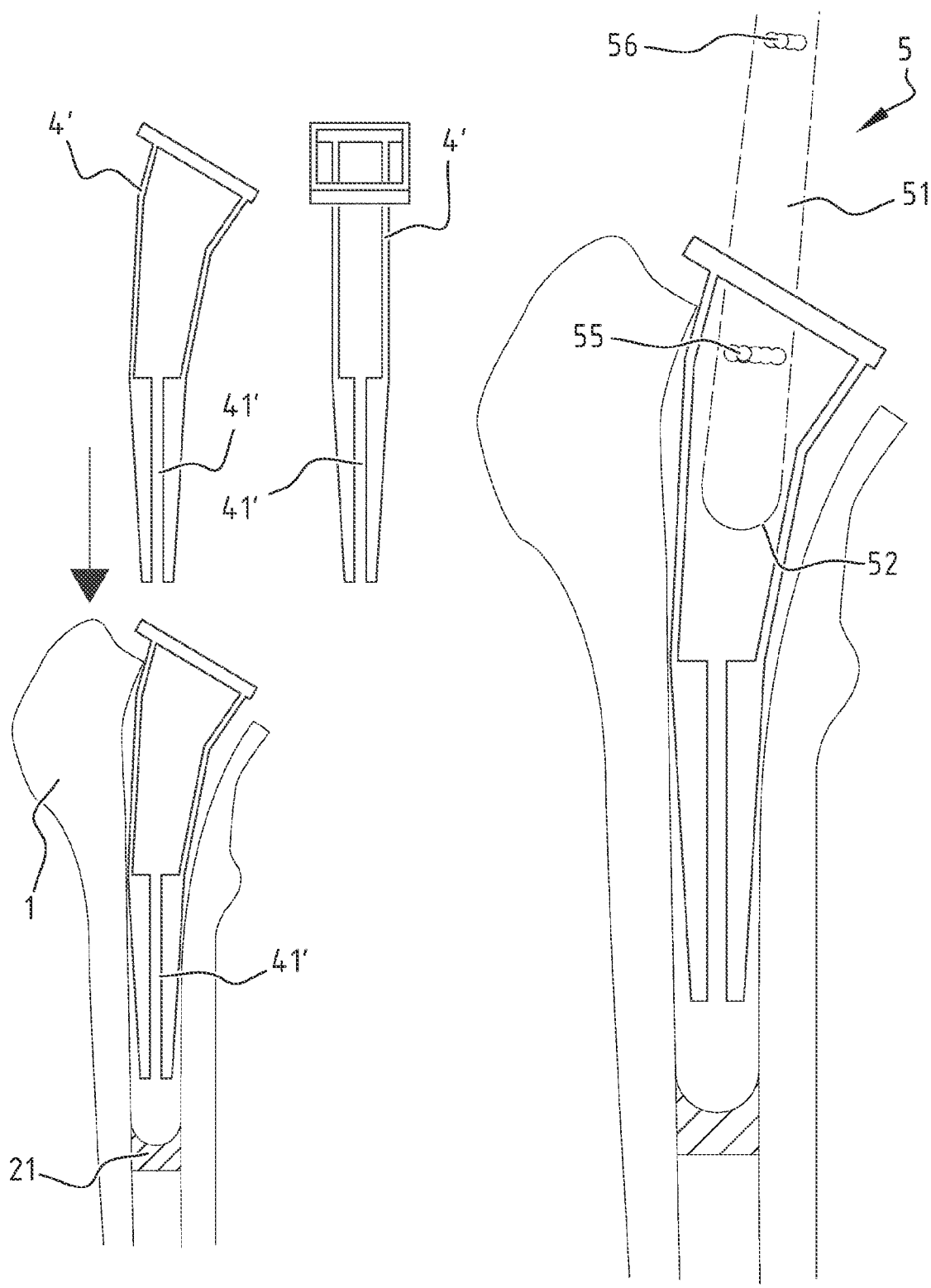
Figure 7G:
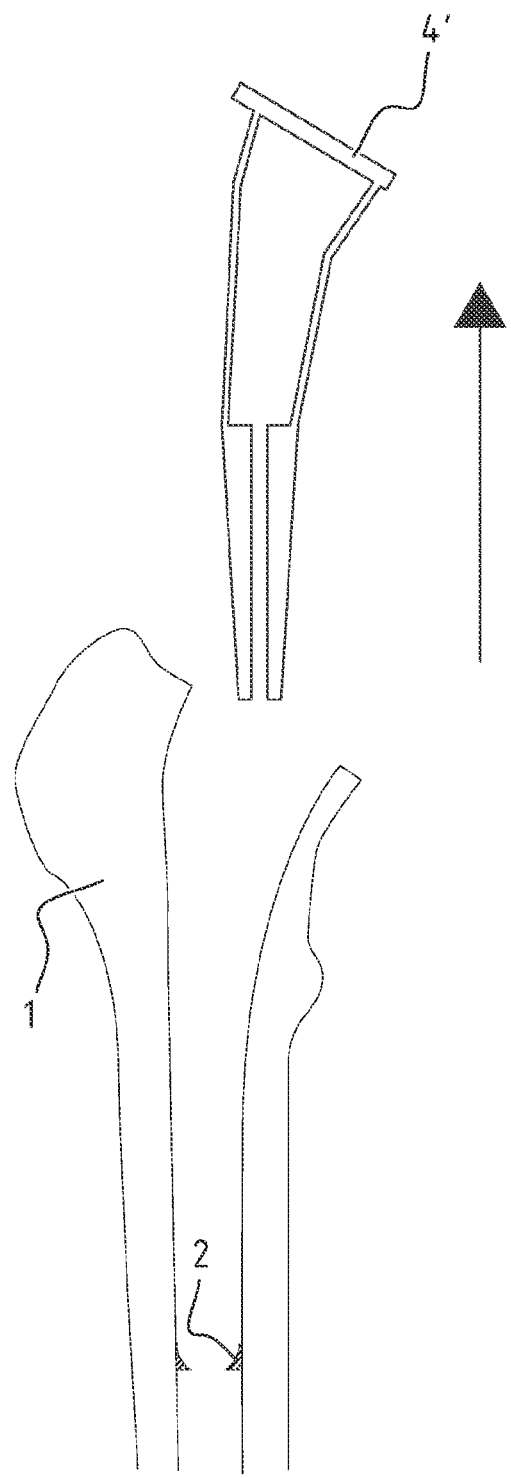
Figure 8A:
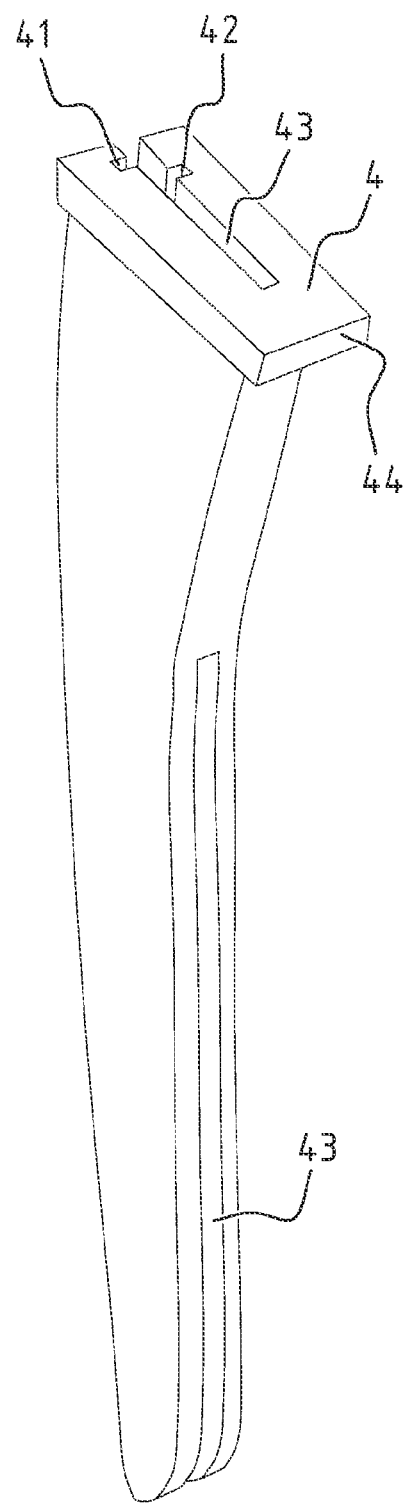
Figure 8B:
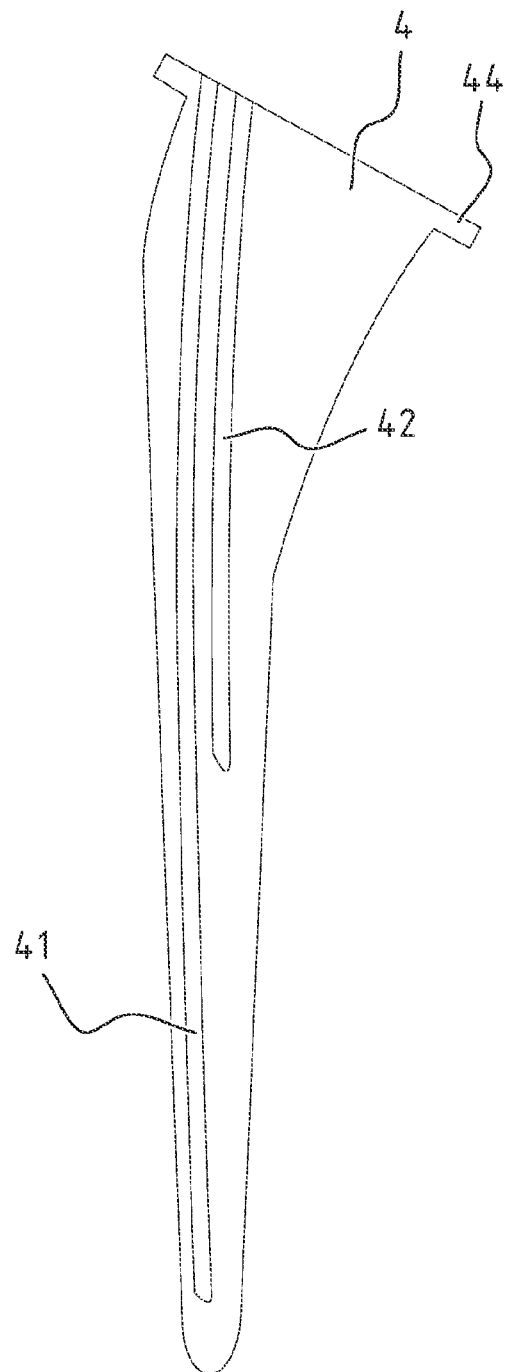
Figure 9A:
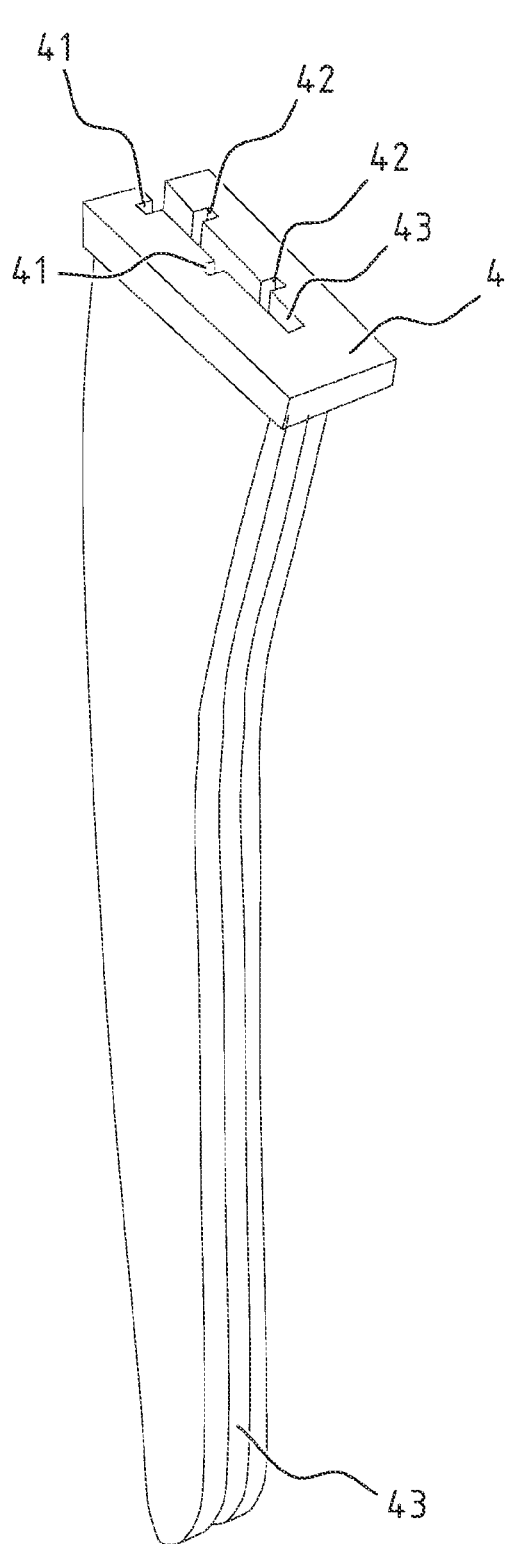
Figure 9B:
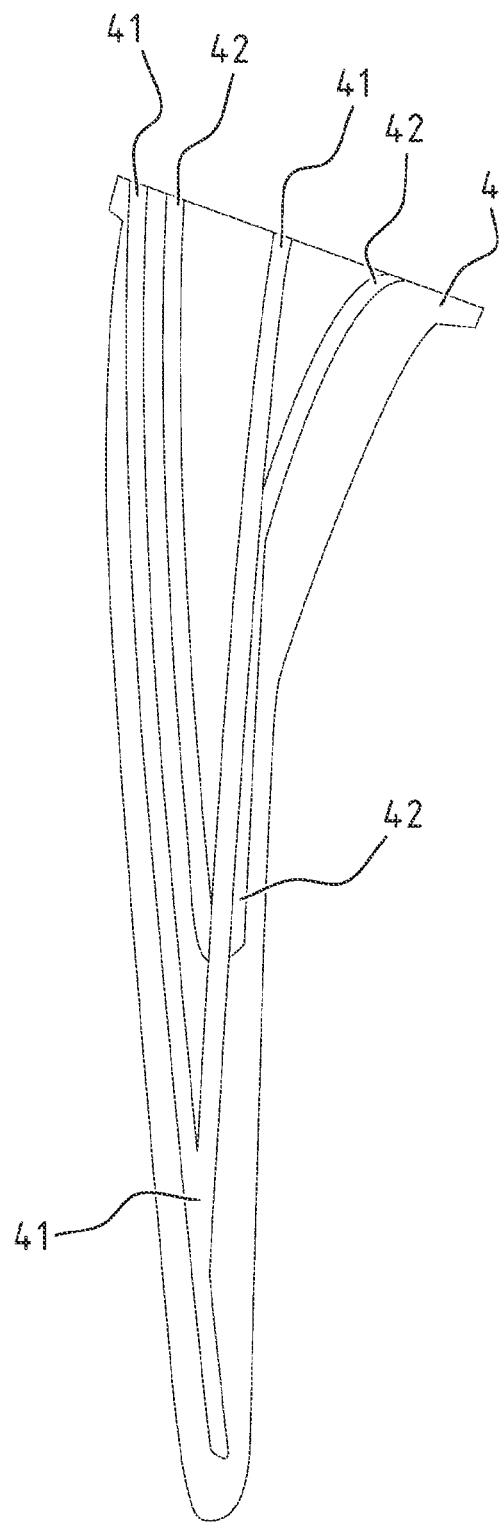
Figure 10A:
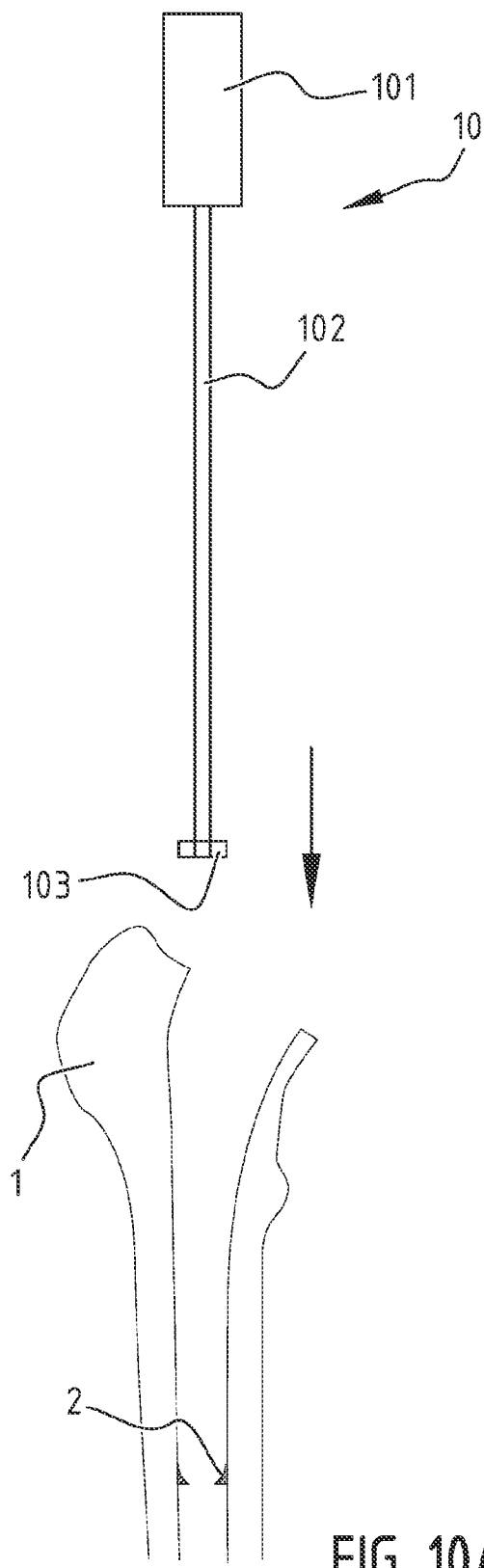
Figure 10B:
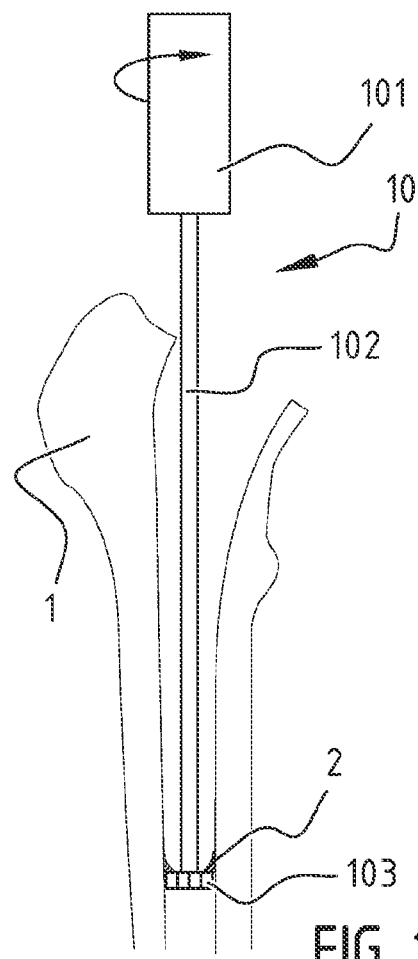
Figure 10C:
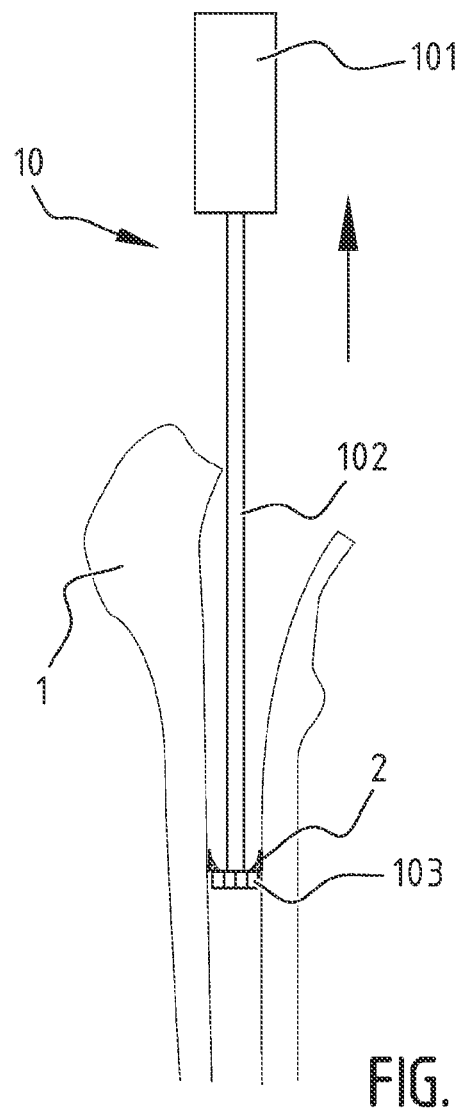
Figure 10D:
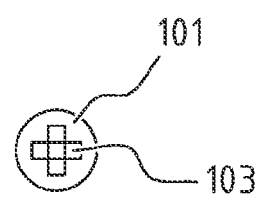

FIGS. 3A-C show screen shots of the process of creating a patient specific guide member on a computer;

FIG. 4 shows a detail of the screen shot of FIG. 3C;

FIG. 5A shows a side view of a detail of a chainsaw blade wherein a laterally extending pin is mounted;

FIG. 5 B shows a front view of a chainsaw wherein two laterally extending pins are mounted on the chainsaw blade;

FIG. 5C shows an alternative embodiment of a chainsaw blade wherein a laterally extending pin is mounted;

FIGS. 6A, B shows the removal of the prosthesis;

FIG. 6C shows the insertion of the guide member in the prosthetic cavity;

FIGS. 6D-G show the insertion of the chainsaw into the guide member;

FIG. 6H shows the chainsaw being pulled out of the guide member;

FIG. 6I shows an alternative embodiment of the patient specific guide member;

FIG. 7A shows the guide member being pulled out of the femur;

FIG. 7B shows the femur after remaining cement is removed from the bone, but leaving the bottom plug;

FIG. 7C shows the insertion of a generic plug cutting guide member in the femur;

FIGS. 7D-E show the insertion of the chainsaw into the generic plug cutting guide member in a first direction;

FIG. 7 F shows the insertion of the chainsaw into the generic plug cutting guide member in a second perpendicular direction;

FIG. 7G shows the generic plug cutting guide member being pulled out of the femur;

FIG. 8A shows a perspective view of the patient specific guide member of FIGS. 3C, 6C-H and 7A;

FIG. 8B shows a cross sectional view of the patient specific guide member of FIG. 8A;

FIG. 9A shows a perspective view of the patient specific guide member of FIG. 6G;

FIG. 9B shows a cross sectional view of the patient specific guide member of FIG. 9A;

FIG. 10A shows a the insertion of a tool for removing the remaining cement pieces of the cement plug in the femur;

FIG. 10B shows the rotation of the tool in the femur for engaging the cement pieces of the cement plug;

FIG. 10C shows the tool with the remaining pieces of the cement plug being pulled out of the femur; and FIG. 10D shows a bottom view of the tool for removing the remaining cement pieces of the cement plug.

The femoral stem of a prosthesis 3 is held in place in the femur of a patient by a cement 2, which is normally polymethylmethacrylate (PMMA). If the prosthesis 3 has to be removed for any reason it can normally be pulled relatively easily from the cement 2 leaving a closed end tubular cement plug 22 within the bone 1 which must then be removed to allow a fresh prosthesis 3 to be inserted and re-cemented.

In the process of removing the prosthetic cement 2, the present invention allows it to be cut to the depth of the cement 2 in a longitudinal line without cutting into the bone 1. Normally three or four of such cuts are made so as to be spaced apart around the perimeter of the cavity.

According to FIG. 1 the area of a prosthesis 3 and the femur 1 of a patient 7 with a cemented total hip arthroplasty, which should undergo revision surgery, is being scanned by a CT scanner 8. As shown in FIG. 2A the scans of a multitude of planes of intersection of the prosthesis 3 and the bone cement 2 are then projected on a computer screen 9 and a virtual 3D model (shown on the right) of the prosthesis 3, the bone 1 and the bone cement 2 is made from said scans. FIG. 2B shows the prosthesis 3 and its dimensions, which may be derived from the virtual 3D model, but which may also be determined by determining the manufacturer and the type of the prosthesis 3.

The cement 2 to be removed is cut by an electrical chainsaw 5 as shown FIG. 5A, 5B and for instance in FIGS. 6D-G. The chainsaw 5 comprises a blade 51, a driven cutting chain 52, a grip 53 and a power button 54. Two pins 55, 56, to be engaged by the guiding grooves 41, 42 of the guide members 4, are mounted on the blade 51, one pin 55 near the bottom end of the blade 51 and one pin 56 at a higher point on the blade 51, more near the center of the length of the blade 51. As shown in FIG. 5B the pin 55 at the bottom end and the pin 56 at the higher point preferably extend at opposite sides of the blade 51. As shown in FIG. 5A the pins 55, 56 can be fixed to the chainsaw blade in several different mutually adjacent holes 57 which are distributed along the width of the blade 51, so as to accommodate a wide variety of distances A and B, corresponding to a wide variety of possible cement thicknesses. FIG. 5C shows an alternative embodiment, wherein the pins 55, 56 are mounted in a rotatable disc 58, to achieve the same.

FIGS. 3A-C show screen shots of the process of designing a patient specific guide member 4 from a scan. First in FIG. 3A the shape and location of the stem of the prosthesis 3 is determined, which determines the shape and location that the guide member 4 will have during removal of the cement. Then in FIG. 3B the profile of the line of intersection of the prosthetic cement/bone interface on the left side of the guide member 4 (shown as a dashed line on the left side of the cement 2) is determined from the scan. As shown in FIG. 3C the shape of the two grooves 41, 42 are determined such that the chainsaw 5 will be guided in the correct manner along the line of intersection of the prosthetic cement/bone interface. Generally the distance A as shown in FIG. 4 between the groove 41 for guiding the bottom end of the chainsaw 5 and the line of intersection of the prosthetic cement/bone interface should be equal to the distance B between the pin 55 and the cutting edge of the chainsaw 5 as shown in Figure SA. The shape of the groove 42 for guiding the higher end of the chainsaw blade 5 prevents rotation of the chainsaw 5 and should be designed such that the cutting edge of the chainsaw's cutting chain 52 is forced to follow exactly the designed path (i.e. the line of intersection of the prosthetic cement/bone interface). As shown in FIGS. 8A, B the guide member 4 is further designed to be provided with a flange 44 extending laterally from the top side for abutment against the top of the femur. A slot 43 for accommodating the blade 51 of the chainsaw 5 is provided in the guide member 4 from the top to the bottom thereof. The slot 43 may split the guide member in two halves, which are then held together by at least the flange 44. In an alternative embodiment, if the guide member is made of a material that can be cut by the chainsaw, such as plastic, the slot 43 may not be (fully) present in the guide member 4 before the chainsaw 5 makes the cut through the cement, in which case the slot 43 is made by the chainsaw 5 during said cutting.

The so designed guide member 4 is then produced, preferably by means of a 3D printer. Materials to print the guide member 4 are for example metal or plastic.

FIG. 6A shows the femur 1, with the prosthesis 3 fixed to the femur 1 by the cement 2. Below the stem of the prosthesis 3 the cement 2 has formed a plug 22. In FIG. 6B the prosthesis is removed from the cement 2. FIG. 6C shows the insertion of the guide member 4 in the prosthetic cavity. Then, while the chainsaw 5 is turned on for cutting, the pin 55 is inserted in the groove 41, then the pin 56 is inserted in the groove 42, and then the chainsaw is moved to the bottom of the cavity until it reaches the plug 21. The chainsaw 5 may or may not be able to cut entirely through the plug 21. FIG. 6H shows the situation where the chainsaw 5 is withdrawn from the cavity without entirely cutting through the plug 22, thereby leaving the plug 22 in place for later removal.

The process as shown in FIGS. 6C to 6H is then repeated three times, at 90 degrees angular intervals and with different patient specific guide members 4 designed for that line of intersection of the prosthetic cement/bone interface, such that the tubular body of cement 2 is cut in four sections.

FIGS. 6I, 9A and 9B show an alternative embodiment of the patient specific guide member 4, wherein the grooves 41, 42 are designed such that the saw can cut the cement 2 along the line of intersection of the prosthetic cement/bone interface on both the left side and the right side of the guide member 4. This results in the grooves 41, 42 being substantially V-, Y- or U-shaped. In this example the groove 41 has a Y-shape, and the groove 42 has a V-shape. In this embodiment the tubular body of cement 2 can be cut into four sections by means of only two different guide members 4.

FIG. 7A shows the guide member 4 being pulled out of the femur, leaving the four sections of cement 2 as a result of the cuts 6 made with the chainsaw 5. The sections of cement 2 are then removed in a conventional way by means of an osteotome (a surgical chisel). FIG. 7B shows the femur 1 after remaining cement is removed from the bone, but leaving the bottom plug 22.

For cutting the plug 22 a generic plug cutting guide member 4' may be used, which has a shape which is generally the same as the stem of the prosthesis 3, and which has two sets of grooves 41', 41'' shaped such that the chainsaw 5 is guided straight down to the plug 22 in two mutually perpendicular orientations of the chainsaw, as shown in FIGS. 7D and 7F. FIGS. 7D-E show the insertion of the chainsaw 5 into the generic plug cutting guide member 4' in a first direction, with the pins 55, 56 being guided in the first grooves 41' to make a first cut through the plug 22, and FIG. 7F shows the insertion of the chainsaw 5 into the generic plug cutting guide member 4' in a second perpendicular direction, with the pins 55, 56 being guided in the second grooves 41'' for making a second perpendicular cut through the plug 22. Then, after the guide member 4' is removed, the remaining cement parts can be easily removed.

According to FIGS. 10A-D the remaining prosthetic cement pieces of the plug 2 are removed by means of a tool 10 comprising an elongated stem 102, a hook 103, and a grip 101. As shown in FIG. 10D, the hook has an X-shaped cross section, seen from below, wherein the four legs of said X-shape extend laterally from the outer end of the stem 102 at 90 degrees intervals. The hook 103 is inserted through the X-shaped opening made by the first and second cuts as described above with reference to FIGS. 7C-G, until the hook 103 extends below the pieces of said plug 2. Then the stem 102 is rotated around its axis by approximately 45 degrees such that the hook 103 engages the bottom surface of the remaining pieces. Then the tool 10 is forcibly moved upwards, by pulling the grip 101 or if necessary by means of hammering against the lower end of the grip 101, thereby removing all four remaining pieces of the plug 2.

The invention has thus been described by means of preferred embodiments. It is to be understood, however, that this disclosure is merely illustrative. Various details of the structure and function were presented, but changes made therein, to the full extent extended by the general meaning of the terms in which the appended claims are expressed, are understood to be within the principle of the present invention. The description and drawings shall be used to interpret the claims. The claims should not be interpreted as meaning that the extent of the protection sought is to be understood as that defined by the strict, literal meaning of the wording used in the claims, the description and drawings being employed only for the purpose of resolving an ambiguity found in the claims. For the purpose of determining the extent of protection sought by the claims, due account shall be taken of any element which is equivalent to an element specified therein. An element is to be considered equivalent to an element specified in the claims at least if said element performs substantially the same function in substantially the same way to yield substantially the same result as the element specified in the claims.

The invention claimed is:

1. A tool system comprising a guide member and cutting tool for removing prosthetic cement from a bone of a patient undergoing a joint prosthesis replacement operation,
   wherein the cutting tool is configured for forming a running cut substantially completely through the prosthetic cement along a line of intersection, wherein at least one profile of the line of intersection of a prosthetic cement/bone interface at its intersection with a generally longitudinally pre-selected plane is obtained by scanning the patient in the area of the joint prothesis;
   wherein the cutting tool has dimensions to be inserted into the prosthetic cavity at least substantially to the bottom end thereof and comprises;
      a cutting element arranged to cut the prosthetic cement at one outer end of said cutting tool; and
      two guiding pins, which guiding pins are located on the cutting tool at a mutual distance apart; and
   wherein the guide member is substantially shaped as a stem of the prosthesis in the prosthetic cavity located in the prosthetic cement; and
   wherein the guide member is provided with two longitudinally running guiding grooves which each are arranged to engage one of said guiding pins of the cutting tool, wherein the guiding grooves are profiled such that the outer end of the cutting tool at which the cutting element is arranged to cut the prosthetic cement, when inserted into the prosthetic cavity and being moved to at least substantially to the bottom end thereof, is forced to follow a path corresponding to the profile of the line of intersection of the cement/bone interface.

2. The tool system of claim 1, wherein the guiding pins extend laterally of the cutting tool, and the two guiding grooves are provided in opposite sides of the guide member.

3. The tool system of claim 1, wherein the two guiding groves run at a distance from each other in the pre-selected plane for preventing rotation of the cutting tool.

4. The tool system of claim 1, wherein the guiding grooves are substantially U-, V-or Y-shaped, wherein the guiding grooves are profiled such that the outer cutting end of cutting element, when inserted into the prosthetic cavity and being moved to at least substantially to the bottom end thereof, wherein the guiding pins move through first ones of said legs of said U-, V-or Y-shaped grooves, and back to the upper end thereof, wherein the guiding pins move through the other legs of said U-, V-or Y-shaped grooves, is forced to follow a substantially U-shaped path corresponding to the profile of the line of intersection of the cement/bone interface on two opposite sides of the intersection.

5. The tool system of claim 1, wherein the cutting tool comprises a chainsaw blade and the cutting element comprises a driven cutting chain, provided with the two guiding pins on the chainsaw blade.

6. The tool system of claim 1, wherein the cutting tool is a small electrical chainsaw provided with the two guiding pins on the chainsaw blade.

7. The tool system of claim 6, wherein the position of at least one of the guiding pins on the chainsaw blade is adaptable in the direction of the side edges of the chainsaw blade, so as to accommodate for both relatively deep and shallow cement cuts.

8. The tool system of claim 6, wherein the chainsaw blade has a wedge shape, wherein the outer end where the cutting chain is arranged to cut is the widest end of the wedge shaped chainsaw blade.

9. The tool system of claim 1, wherein the cutting tool further comprises a grip arranged on the other outer end of the cutting tool for engagement of the cutting tool by an operator.

10. The tool system of claim 1, wherein said guide member is produced by means of a 3D-printer.

11. A tool system comprising a guide member and cutting tool for removing prosthetic cement from a bone of a patient undergoing a joint prosthesis replacement operation,
wherein the cutting tool is configured for forming a running cut substantially completely through the prosthetic cement along a line of intersection, wherein at least one profile of the line of intersection of a prosthetic cement/bone interface at its intersection with a generally longitudinally pre-selected plane is obtained by scanning the patient in the area of the joint prothesis;
wherein the guide member is substantially shaped as a stem of the prosthesis in the prosthetic cavity located in the prosthetic cement; and
wherein the guide member and the cutting tool are shaped to engage with each other such that an outer end of the cutting tool at which the cutting is performed, when inserted into the prosthetic cavity and being moved to at least substantially to the bottom end thereof, is forced to follow a path corresponding to the profile of the line of intersection of the cement/bone interface.

* * * * *